United States Patent [19]
Gormley et al.

[11] Patent Number: 6,124,490
[45] Date of Patent: Sep. 26, 2000

[54] ZWITTERIONIC SILOXANE POLYMERS AND IONICALLY CROSS-LINKED POLYMERS FORMED THEREFROM

[75] Inventors: John L. Gormley, Midland Park; Abe Berger, Summit; Dennis L. Fost, Ridgwood, all of N.J.

[73] Assignee: Mona Industries, Inc., Paterson, N.J.

[21] Appl. No.: 09/427,216

[22] Filed: Oct. 26, 1999

[51] Int. Cl.$^7$ ........................................................ C07F 7/10
[52] U.S. Cl. .......................... 556/425; 556/413; 556/418; 548/406; 528/12; 528/20; 528/25; 528/27; 528/28; 514/864; 106/287.11; 106/287.14; 106/287.15; 424/401; 424/447; 424/449; 424/60; 424/65; 424/64; 424/70.2; 424/7.12; 424/70.122; 424/49; 510/122; 510/130
[58] Field of Search ....................................... 556/413, 425, 556/418; 548/406; 528/12, 20, 25, 27, 28; 514/844; 106/287.11, 287.14, 287.15; 424/401, 447, 449, 60, 65, 64, 70.2, 70.12, 70.122, 49; 510/122, 130

[56] References Cited

U.S. PATENT DOCUMENTS

| | | |
|---|---|---|
| 3,956,353 | 5/1976 | Plueddemann . |
| 4,493,926 | 1/1985 | Williams, Jr. et al. . |
| 4,496,705 | 1/1985 | Florence et al. . |
| 4,525,567 | 6/1985 | Campbell et al. . |
| 4,654,161 | 3/1987 | Kollmeier et al. . |
| 4,898,614 | 2/1990 | Halloran et al. . |
| 4,918,210 | 4/1990 | Fenton et al. ............................ 556/425 |
| 5,008,424 | 4/1991 | Halloran et al. . |
| 5,194,251 | 3/1993 | Halloran et al. ..................... 556/425 X |
| 5,336,419 | 8/1994 | Coffindaffer et al. ............... 556/425 X |
| 5,654,362 | 8/1997 | Schulz, Jr. et al. . |
| 5,665,804 | 9/1997 | Hill et al. . |
| 5,733,529 | 3/1998 | Hill et al. .................................. 424/49 |
| 5,990,334 | 11/1999 | Hierstetter et al. ..................... 556/413 |

FOREIGN PATENT DOCUMENTS

WO 97/36573  10/1997  WIPO .

*Primary Examiner*—Paul F. Shaver
*Attorney, Agent, or Firm*—Franklyn Schoenberg; Norman E. Lehrer

[57] ABSTRACT

Ionically cross-linked silicone polymers of a thickened gel-like consistency are made by reacting a diamino containing polysiloxane with an acid containing reactant selected from itaconic acid or the ester derivative thereof; substituted or unsubstituted cyclic and ankydride; substituted or unsubstituted conjugated olefinic acid or mixtures of the same at an elevated temperature in the presence of a low molecular weight silicone oil or other solvent until an ionically cross-linked zwitterionic siloxane polymer of a gel-like consistency is formed.

16 Claims, No Drawings

ZWITTERIONIC SILOXANE POLYMERS AND IONICALLY CROSS-LINKED POLYMERS FORMED THEREFROM

FIELD OF THE INVENTION

This invention is directed to zwitterionic siloxane polymers and more particularly to zwitterionic siloxane polymers and ionically cross-linked modified aminofunctional polysiloxane polymers of a gel-like consistency used to thicken silicone oils or other solvents. Cross-links are junctions of polymer strands in a three-dimensional network. Ionic cross-links are preferred because the final gel viscosity may also depend on temperature and ionic strength, thereby allowing additional post-processing to occur.

BACKGROUND OF THE INVENTION

A variety of zwitterionic containing silanes and siloxane polymers are known and the use of some of them have been found to provide ionic cross-linking with the formation of siloxane gels and solid rubbers. The siloxane polymers which have heretofore been disclosed as forming gels by virtue of ionic cross-linking, however, require the use of particular reagents because of the difficulty and cost of making polymers which would enable sufficient cross-linking to achieve gels and solid rubbers.

For example, a type of elastomeric silicone zwitterionomers are disclosed in U.S. Pat. No. 4,525,567, issued Jun. 25, 1985, to Campbell et al. The zwitterionomers disclosed which exhibit ionic cross-linking and form gels or solid rubber are characterized as being sultone based zwitterionomers whereas in contrast thereto the composition of the present invention are sulfur free, amic-acid or pyrrolidone carboxy based zwitterionomers. A further distinction exists between the Campbell et al products and the instant invention wherein the reactions may be conducted in the presence of silicone oils or other preferred solvents.

In U.S. Pat. No. 3,956,353, issued May 11, 1976 to Plueddemann, there is disclosed the reaction product of an aminofunctional silane and a cyclic acid anhydride. These reactants are limited, however, to vinyl benzyl functional amines which differ from the amine functional groups of the reactants of the present invention nor is there required such a substitution. Moreover, the products disclosed in the patent are low molecular weight monomers which are aqueous or alcohol coupling agent compositions, in contrast to the thickening compositions disclosed in the present invention.

In U.S. Pat. No. 5,008,424, Halloran et al., disclose zwitterionic aminofunctional siloxanes based on the reaction product of an aminofunctional siloxane and a cyclic acid anhydride for use in polish formulations. However, Halloran et al. discloses only low to medium molecular weight fluids and furthermore does not make mention of high molecular weight Zwitterionic fluids or the solvent thickening properties thereof.

U.S. Pat. No. 5,654,362, Schulz et al. disclose silicone oils and solvents thickened by utilizing cross-linked silicone elastomers, particularly the reaction of silicone hydride containing fluid with alpha, omega-diene catalyzed by platinum in the presence of a low molecular weight silicone oil. The present invention differs in that a zwitterionically cross-linked system is formed by inter and/or intra molecular non-covalent junctions. Schulz et al. further requires the gel to be mechanically forced under shear into a paste or powder when additional low molecular weight oil is added. Unlike Schulz et al., in the present invention, gel consistency is related in part to temperature and additional silicone oils or solvents may be added with heating when further dilution is required.

As such, the present invention provides new and unique advantages over typical prior art for thickened silicone oil formulations which will become apparent hereinafter.

BRIEF SUMMARY OF THE INVENTION

Our invention relates to new ionically cross-linked polysiloxane compositions of a thickened gel-like consistency prepared by reacting (A), a diamino containing polysiloxane of the general formula (Formula 1):

Formula 1

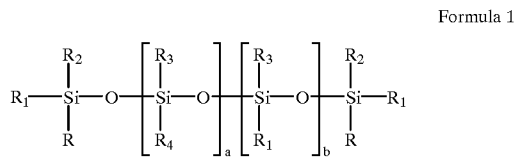

wherein:

R, which can be the same or different, is selected from $R_2$ or $-OR_9$, wherein $R_9$ is hydrogen or alkyl;

$R_1$ can be the same or different, and can be selected from R, $R_2$ or a diamino containing radical of the formula $-F_1-NR_5-F-NH_2$, wherein $F_1$ is linear or branched alkylene of 1–12 carbon atoms; F is linear or branched alkylene of 2–10 carbon atoms and $R_5$ is hydrogen or lower alkyl; with the proviso that at least one $R_1$ group is a diamino containing radical;

$R_2$ can be the same or different and can be selected from R, and substituted or unsubstituted alkyl, aryl and olefinic (vinyl);

$R_3$ and $R_4$, which can be the same or different, can be selected from substituted or unsubstituted alkyl, aryl, capped or uncapped polyoxyalkylene, alkaryl, aralkylene or alkenyl;

a is an integer from 0 to 10,000; and b is an integer from 10 to 1000; with the proviso that if the pendant $R_1$ group is a diamino containing radical, a can be o or a and b are present in a ratio of a:b of at least 1:1 to 200:1;

with (B), an acid containing reactant selected from itaconic acid and/or the trialkylsilyl ester derivatives thereof; substituted or unsubstituted cyclic acid anhydride; substituted or unsubstituted conjugated olefinic acid such as acrylic acid or ester thereof or vinyl phosphoric acid, and mixtures of the same, at an elevated temperature (preferably from about 25° C. to about 150° C.), to form an ionically cross-linked zwitterionic siloxane polymer of a thickened gel-like consistency containing both carboxylic acid and secondary and/or tertiary amino radicals. Optionally, the reaction is carried out in the presence of (C) a low molecular weight silicone oil or other solvents, which additionally comprises new methods of thickening silicone oils or other solvents to gel-like consistency.

The ionically cross-linked polysiloxane compositions of the invention comprise a zwitterionic siloxane polymer composition component (hereinafter referred to as "ionomer") which is represented by the Formula 2:

Formula 2

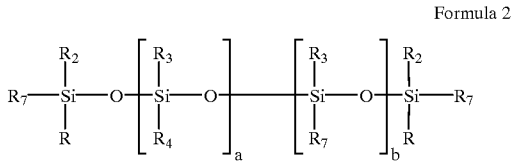

wherein:

$R_1$, $R_2$, $R_3$, $R_4$, a and b are as hereinabove defined; and
$R_7$, which can be the same or different, can be selected from R, $R_2$ or a group select from group (a), (b) or (c) below, with the proviso that at least one $R_7$ group is selected from:

(a) a pyrrolidone containing group of the general structure represented by the Formula 3 if itaconic acid or ester thereof is reacted with the primary amine of the diamine group;

Formula 3

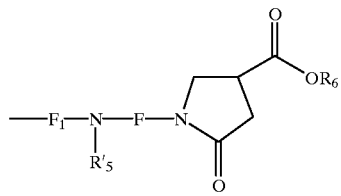

wherein:

$R'_5$ is hydrogen lower alkyl or a group of Formula 3a, with the proviso that it more than one equivalent of itaconic acid or ester thereof is charged to the reaction mixture containing composition of formula 1, $R'_5$ can include a group of the Formula 3a:

Formula 3a

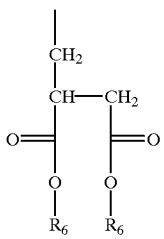

wherein:

$R_6$ is OH, OM or trialkylsiloxy, wherein M is a cation; and
$F_1$ and F are as hereinabove defined;

(b) a group of the general structure represented by Formula 4, if about one equivalent of a cyclic anhydride reactant is used;

Formula 4

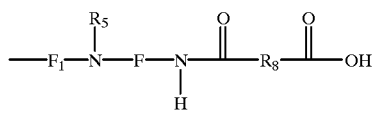

wherein:

$R_5$ is hydrogen or lower alkyl;
$R_8$ is a substituted or unsubstituted, branched or unbranched alkylene radical, preferably ethylene, propylene, ortho phenylene or unsaturated alkylene radicals such as vinylidene; and
$F_1$ and F are as hereinabove defined; and (c) a group of the general structure of Formula 5 if a conjugated olefinic acid is used:

Formula 5

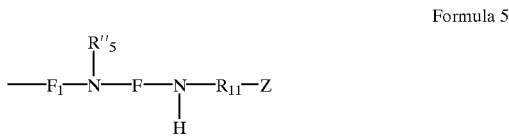

wherein:

$R''_5$ is hydrogen, lower alkyl or a group of Formula 5a, with the proviso that if more than one equivalent of conjugated olefinic acid was charged to the reaction mixture containing formula 1, $R''_5$ can include a group of Formula 5a.

$$—R_{11}—Z$$ Formula 5a $R_{11}$ is ethylene or substituted ethylene;
Z is selected from $—CO_2H$ or $—SO_3H$;
F, $F_1$ are as hereinabove defined.

The ionically cross-linked polysiloxane compositions of the invention comprise at least 5 percent by weight of a low molecular weight silicone oil, preferably a volatile silicone oil, although nonvolatile silicone oils and/or non-silicone containing solvents can also be used.

In yet another aspect of the present invention there is provided an alternate method for preparing zwitterionic silicone polymers suitable for forming ionically cross-linked polysiloxane gels by reacting (A) an organosilicone hydride containing fluid or composition having one or more terminal or lateral hydrides on the polysiloxane chain with (B) a terminal alkenyl containing pyrrolidone ester represented by Formula 6 wherein the alkylene linkage is interrupted by a secondary or tertiary amino group:

Formula 6

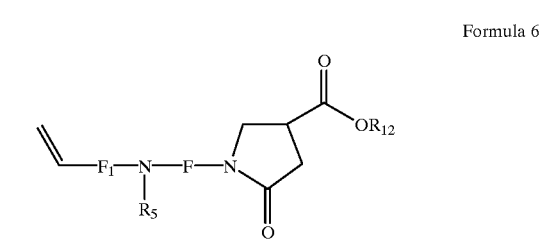

wherein:

$R_5$ is hydrogen or lower alkyl;
$R_{12}$ is a trialkylsilyl ester; and
$F_1$ and F are as hereinabove defined;

(C) in the presence of a noble metal catalyst, preferably soluble platinum, at an elevated temperature (preferably between about 65° C. and 130° C.) for the time sufficient to react, preferably substantially completely react, the hydride groups on the silicone fluid or composition with the olefinic pyrrolidone ester; and (D) optionally in the presence of a low molecular weight silicone oil, followed by hydrolyzing the trialkylsilyl ester(s) to form the zwitterionomer.

In a further embodiment, the ionically cross-linked silicone gel can be mixed with additional low molecular weight silicone oils or other solvents and/or cosmetic or other ingredients optionally with heating to produce formulated products.

These and other objects of our invention will become apparent from a consideration of the following detailed description.

DESCRIPTION OF THE PREFERRED EMBODIMENTS

Ionically cross-linked polysiloxane compositions of a gel-like consistency are prepared by forming ionic cross-links between amino and carboxyl containing zwitterionic polysiloxanes (ionomers) in the presence of a low molecular weight linear or cyclic polysiloxane. The silicone ionomer containing compositions can optionally be diluted with additional low molecular weight polysiloxane with heating. Suitable silicone compositions containing from 5 to 95 percent by weight, preferably from 5 to 25 percent by weight, of ionically cross-linked zwitterionic polysiloxanes, and from 95 to 5 weight percent, preferably 95 to 75 weight percent, of other ingredients, particularly low molecular weight volatile and non-volatile silicones and other solvents as hereinafter described form uniform silicone gels with a wide viscosity range. The silicone gels have excellent properties including clarity, thixotropy, shear thinning, thermoplasticity and can spread smoothly on the skin, They can be applied in cosmetic and medical products as the base oil. The silicone ionomer containing compositions of the present invention have the unique property of being easily rubbed-in on the skin, providing improved substantivity and water resistance. These materials are also ideal for use in solid cosmetics such as antiperspirants and deodorants as well as being suitable for use in applications requiring increased durability and performance from industrial silicones.

The new ionically cross-linked polysiloxane compositions of the invention can be prepared by reacting (A) a capped or uncapped diamino containing polysiloxane of the general formula (Formula 1):

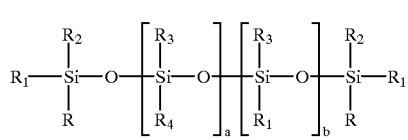

Formula 1 wherein:

R, which can be the same or different, is selected from $R_2$ or —$OR_9$, wherein $R_9$ is hydrogen or alkyl;

$R_1$ can be the same or different and can be selected from R, $R_2$ and a diamino containing radical of the formula —$F_1$—$NR_5$—F—$NH_2$; with the proviso that at least one $R_1$ group is a diamino containing radical wherein; $F_1$ is linear or branched alkylene of 1–12 carbon atoms, preferably propylene and isobutylene; F is linear or branched alkylene of 1–10 carbon atoms, preferably ethylene, and $R_5$ is hydrogen or lower alkyl;

$R_2$ can be the same or different and can be selected from R or substituted or unsubstituted alkyl, aryl and olefinic (vinyl);

$R_3$ and $R_4$, which can be the same or different, are selected from substituted or unsubstituted alkyl, aryl, capped or uncapped polyoxyalkylene, alkarylene, aralkylene or alkenyl;

a is an integer from 0 to 10,000; and b is an integer from 10 to 1000; with the proviso that when a pendant $R_1$ group is a diamino containing radical, a can be 0 or a and b are present in the ratio of a:b of at least 1:1 to about 200:1, preferably from 10:1 to 100:1, most preferably from 15:1 to about 25:1 with (B), an acid containing reactant such as itaconic acid and/or the trialkylsilyl ester derivatives thereof, substituted or unsubstituted cyclic acid anhydrides, or substituted or unsubstituted conjugated olefinic acid, and mixtures of the same, at an elevated temperature, preferably from about 25° C. to about 150° C., to form an ionically cross-linked zwitterionic siloxane polymer of a gel-like consistency containing both carboxylic acid and secondary and/or tertiary amino radicals. The reaction is carried out in the presence of a low molecular weight silicone oil or other solvents, which additionally comprises new methods of thickening silicone oils or other solvents to gel-like consistency.

The ionically cross-linked polysiloxane compositions of the invention comprises a capped or uncapped zwitterionic siloxane polymer component of the invention represented by the Formula 2:

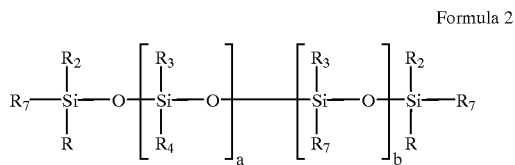

Formula 2 wherein:

R, $R_2$, $R_3$, $R_4$, $R_9$, a and b are as hereinabove defined; and $R_7$, which can be the same or different, can be selected from $R_1$ or a group selected from (a), (b) or (c) below, with the proviso that at least one $R_7$ group is selected from:

(a) a pyrrolidone containing group of the general structure represented by the formula 3 if about one equivalent of itaconic acid or ester thereof is reacted with the primary amine of the diamine group:

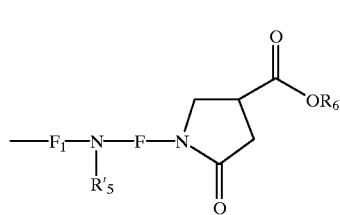

Formula 3 wherein:

$R'_5$ is hydrogen, lower alkyl or a group represented by Formula 3a, with the proviso that if more than one equivalent of itaconic acid or ester thereof is charged to the reaction mixture containing formula 1, $R'_5$ can include a group represented by Formula 3a.

Formula 3a

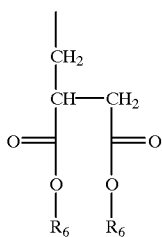

wherein:
R$_6$ is OH, OM or trialkylsiloxy, wherein M is a cation such as alkaline earth metal, alkali metal, ammonium or substituted ammonium salt; and
F$_1$ and F are as hereinabove defined;
(b) a group of the general structure represented by Formula 4, if about one equivalent of a cyclic anhydride reactant is used;

Formula 4

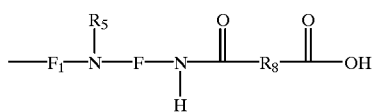

wherein:
R$_8$ is a substituted or unsubstituted, branched or unbranched alkylene radical, preferable ethylene, propylene, ortho phenylene or unsaturated alkylene radicals such as vinylidene;
R$_5$ is hydrogen or lower alkyl; and
F$_1$ and F are as hereinabove defined; and
(c) a group of the general structure of Formula 5 if about one equivalent of conjugated olefinic acid is used;

Formula 5

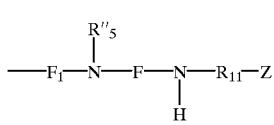

wherein:
R''$_5$ is hydrogen, lower alkyl or a group represented by Formula 5a, with the proviso that if more than one equivalent of conjugated olefinic acid was charged to the reaction mixture containing formula 1, R''$_5$ can include a group represented by Formula 5a;

—R$_{11}$—Z  Formula 5a wherein:
R$_{11}$ is ethylene or substituted ethylene;
Z is —CO$_2$H or —SO$_3$H; and
F and F$_1$ are as hereinabove defined.

The novel ionically crosslinked compositions of a gel like consistency containing a capped or uncapped zwitterionic class of polysiloxanes surprisingly and unexpectedly can be readily and directly prepared by the reaction of corresponding capped or uncapped silicone compositions or fluids having one or more functional diamine groups, each of which group must contain a primary amine group, with about stoichiometric quantities, preferably around 0.8 to 1.2 equivalents, of an acid containing reactant including itaconic acid or its ester, substituted or unsubstituted cyclic acid anhydrides and substituted or unsubstituted conjugated olefinic acids, or mixtures thereof, per functional diamine group at an elevated temperature for the time sufficient for substantially all of the acid reactant such as itaconic acid or its ester to react with the functional primary amine group. Preferably the reaction is carried out in the presence of a volatile or non-volatile silicone oil or other solvent. (n general from about 0.5 to about 2.5, preferably from about 0.8 to about 1.2, equivalents of acid reactant such as itaconic acid or its ester per functional primary amine group is reacted with the diamino functional containing silicone fluid wherein, for example, substantially all the itaconic acid and preferably all the functional primary amine group(s) are reacted and a polysiloxane composition with at least one functional carboxyl group such as a pyrrolidone-containing functional carboxyl group(s) and/or its ester or salt is formed.

The reaction can be carried out neat or in up to about 95% by weight of an inert solvent such as low molecular weight linear or cyclic polysilicone oils, alcohol, hydrocarbon solvent, chlorinated hydrocarbon and the like, as desired, at elevated temperatures from 25° C. up to about 175° C., preferably from about 40° C. to about 130° C., with more preferred temperatures depending on the choice of acid reactant. The reaction readily proceeds and the generally complete reaction of the itaconic acid or its ester or other acid reactants herein described with the available functional primary amine groups and including where applicable, cyclization to form a pyrrolidone group will occur in from about 1 to 5 hours. Routine analytical techniques for amine and acid values as well as monitoring viscosity, color and water and/or alcohol evolution can be used to determine completion of the reaction.

Suitable capped or uncapped functional diamine silicone fluids for use in accordance with the practice of the invention, having one or more functional diamine group(s) that contain a primary amine group, and which may be linked terminally, laterally or both terminally and laterally as desired via an alkylene linkage to silicon are well known and are available commercially, for example from Dow Corning, General Electric Witco and Shin-Etsu. Exemplary suitable functional diamine silicone fluids are silicone fluids having one or more aminoalkylaminoalkylene capped functional groups, including, for example, aminoethylaminopropyl functional silicone fluids such as KF 393 from Shin-Etsu and aminoethylaminoisobutyl functional silicone fluids such as X2-8107 and Q2-8220 from Dow Corning. Suitable uncapped silicone fluids include alkoxy or hydroxy terminated silicone fluids such as KF857 from Shin-Etsu, and other methoxy terminated aminoethylamionopropyl functional silicone fluids. While the equivalent weight of the silicone fluids or compositions which may be employed in the preparation of the zwitterionic carboxyl containing functional polysiloxanes of a gel-like consistency of the present invention is not critical, and suitable compositions may have equivalent weights of 10,000 or even higher, although silicone fluids having equivalent weights from about 500 to about 5,000 are in general preferred.

As indicated, the pyrrolidone-containing carboxyl functional zwitterionic polysiloxane component of the composition of the present invention is readily prepared by reaction of diamino functional silicone fluids wherein each of the diamine groups must contain a primary amine with itaconic acid or its ester. Itaconic acid (methylene succinic acid) is a compound of the formula:

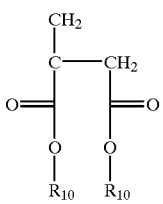

wherein $R_{10}$, which can be the same or different, is hydrogen, lower alkyl (1–6 carbon atoms) or trialkylsilyl.

The compound itaconic acid is available commercially from Rhone Poulenc and Pfizer Chemicals Division whereas ester derivatives thereof are available from Morflex Inc., Greensboro, N.C. The compounds are produced by known fermentation techniques although chemical synthesis methods are also known.

As indicated, zwitterionic polysiloxane containing compositions of a gel-like consistency are also prepared by reacting corresponding capped and uncapped silicone compositions having one or more functional diaminine groups which contain a primary amine group as herein described with a cyclic acid anhydride reactant at an elevated temperature from about 25° C. to about 120° C. in the presence of a low molecular weight volatile and non-volatile silicones or other solvents. However, reaction at temperatures in excess of 75° C. for extended periods of time may negatively alter the product if the amic-acid reaction product formed from the anhydride and the amine begins cyclizing to the imide. Cyclic acid anhydrides which are suitable for reaction with the compositions of formula 1 are selected from the group consisting of succinic anhydride, maleic anhydride, phthalic anhydride, itaconic anhydride, octenyl succinic anhydride, dodecenyl succinic anhydride, octadecenyl succinic anhydride, citricanoic anhydride, dodecyl succinic anhydride, polyisobutylene succinic anhydride or other cyclic anhydrides with succinic anhydride being the preferred material for use herein.

Conjugated olefinic acids also suitable for use as a reactant for preparing zwitterionic polysiloxane containing compositions by the reaction with capped and uncapped silicone compositions having one or more functional diamine groups in the presence of low molecular weight volatile silicones or other solvents at elevated temperatures in accordance with the practice of the present invention include unsaturated carboxylic acids such a acrylic acid, methacrylic acid and crotonic acid.

In another aspect of the present invention there is provided an alternate method for preparing zwitterionic silicone polymers suitable for forming ionically cross-linked polysiloxane gels by reacting an organosilicone hydride containing fluid or composition having one or more terminal or lateral hydrides on the polysilioxane chain with a terminal alkenyl containing pyrrolidone ester represented by Formula 6, particularly the trialkylsilyl ester: wherein the alkylene linkage is interrupted by a secondary or tertiary amino groups such as:

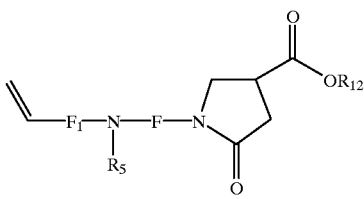

Formula 6 wherein $R_{12}$ is a trialkylsilyl ester; and $F$, $F_1$ and $R_5$ are as hereinabove defined;

in the presence of a noble metal catalyst (Group VIII metal), preferably soluble platinum catalyst, at an elevated temperature (preferably between about 65° C. and 130° C.) for the time sufficient to react, preferably substantially completed react, the hydride groups on the silicone fluid or composition with the olefinic pyrrolidone ester, optionally in the presence of a low molecular weight silicone oil followed by hydrolyzing the trialkylsily ester(s) to form the zwitterionomer.

The low molecular weight silicone oil suitable for use in preparing ionically cross-linked polysiloxane compositions of the present invention having a gel-like consistency are preferably an inert volatile silicone oil, although nonvolatile silicone oils and a variety of non-silicone inert containing solvents can also be used.

The phrase low molecular weight silicone oil is intended to include (i) low molecular weight linear and cyclic volatile methyl siloxanes, (ii) low molecular weight linear and cyclic volatile and non-volatile alkyl and aryl siloxanes, and (iii) low molecular weight linear and cyclic functional siloxanes. Most preferred, however, are low molecular weight linear and cyclic volatile methyl siloxanes (VMS).

VMS compounds correspond to the average unit formula $(CH_3)_a SiO_{(4-a)}/2$ in which "$\alpha$" has an average value of two to three. The compounds contain siloxane units joined by =S—O—Si= bonds. Representative units are monofunctional "M" units, $(CH_3)_3 SiO_{1/2}$, and difunctional "D" units, $(CH_3)_2 SiO$. Difunctional units not specifically made up of dimethyl siloxane are in general referred to D' units.

The presence of trifunctional "T" units, $CH_3SiO_{3/2}$, results in the formation of branched linear or cyclic volatile methyl siloxanes. The presence of tetrafunctional "Q" units, $SiO_{4/2}$, results in the formation of branched linear or cyclic volatile methyl siloxanes.

Linear VMS has the formula $(CH_3)_3SiO\{(CH_3)_2SiO\}_y Si(CH_3)_3$. The value of "y" is 0–5. Cyclic VMS has the formula $\{(CH_3)_2SiO\}_z$. The value of "z" is 3–6. Preferably, these volatile methyl siloxane having boiling points less than about 250° C. and viscosities of about 0.65–5.0 centistokes (mm2/s).

Representative linear volatile methyl siloxanes are hexamethyldisiloxane (MM) with a boiling point of 100° C., viscosity of 0.65 mm²/s, and formula $Me_3SiOSiMe_3$; octamethyltrisiloxane (MDM) with a boiling point of 152° C., viscosity of 1.04 mm²/s and formula $Me_3SiOMe_2SiOSiMe_3$; decamethyltetrasiloxane (MD₂M) with a boiling point of 194° C., viscosity of 1.53 mm²/s, and formula $Me_3SiO(Me_2SiO)_2SiMe_3$; dodecamethylpentasiloxane (MD₃ M) with a boiling point of 229° C., viscosity of 2.06 mm²/s, and formula $Me_3SiO(Me_2SiO)_3SiMe_3$; tetradecamethylhexasiloxane (MD₄M) with a boiling point of 245° C., viscosity of 2.63 mm²/s, and formula $Me_3SiO(Me_2SiO)_4SiMe_3$; and hexadecamethylheptasiloxane (MD₅M) with a boiling point of 270° C., viscosity of 3.24 mm²/s, and formula $Me_3SiO(Me_2SiO)_5SiMe_3$.

Representative cyclic volatile methyl siloxanes are hexamethylcyclotrisiloxane ($D_3$) a solid with a boiling point of 134° C. and formula $\{(Me_2)SiO\}_3$; octamethylcyclotetrasiloxane ($D_4$) with a boiling point of 176° C., viscosity of 2.3 mm²/s, and formula $\{(Me_2)SiO\}_4$; decamethylcyclopentasiloxane ($D_5$) with a boiling point of 210° C., viscosity of 3.87 mm²/s and formula $\{(Me_2)SiO\}_5$; and dodecamethylcyclohexasiloxane ($D_6$) with a boiling point of 245° C., viscosity of 6.62 mm²/s and formula $\{(Me_2)SiO\}_6$. Representative branched volatile methyl siloxanes and are heptamethyl-3-{(trimethylsilyl)}trisiloxane ($M_3T$) with a boiling point of 192° C., viscosity of 1.57 mm²/s, and formula $C_{10}H_{30}O_3Si_4$; hexamethyl-3,3, bis(trimethylsilyl)oxy} trisiloxane ($M_4Q$) with a boiling point of 222° C., viscosity of 2.86 mm²/s, and formula $C_{12}H_{36}O_4Si_5$; and pentamethyl {(trimethylsilyl)oxy}cyclotrisiloxane ($MD_3$) with the formula $C_8CH_{24}O_4Si_4$.

As previously noted, our process also includes using low molecular weight linear and cyclic volatile and non-volatile alkyl and aryl siloxanes. Representative linear polysiloxanes are compounds of the formula $R'_3SiO(R'_2SiO)_ySiR'_3$ and representative cyclic polysiloxanes are compounds of the formula $(R'_2SiO)_z$ wherein R' is an alkyl group of 1–20 carbon atoms, or an aryl group such as phenyl. The value of "y" is 0–80, preferably 0–20. The value of "z" is 0–9, preferably 4–6. These polysiloxanes have viscosities generally in the range of about 1–100 centistokes (mm²/s).

Other representative low molecular weight non-volatile polysiloxanes have the general structure:

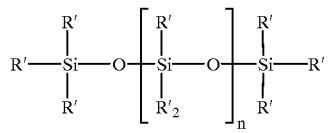

wherein n has a value to provide polymers with a viscosity in the range of about 100–1,000 centistokes (mm²/sec);

R' is as hereinabove defined; and $R'_2$ is an aryl group such as phenyl. Typically, the value of n is about 80–375. Illustrative polysiloxanes are polydimethylsiloxane, polydiethylsiloxane, polymethylethylsiloxane, polymethylphenylsiloxane, and polydiphenylsiloxane Low molecular weight functional polysiloxanes can be represented by acrylamide functional siloxane fluids, acrylate functional siloxane fluids, amide functional siloxane fluids, amino functional siloxane fluids, carbinol functional siloxane fluids, carboxyl functional siloxane fluids, chloroalkyl functional siloxane fluids, glycol functional siloxane fluids, ketal functional fluids, mercapto functional siloxane fluids, methyl ester functional siloxane fluids, perfluoro functional siloxane fluids and silanol functional siloxanes.

Our invention is not limited to ionically cross-linked polysiloxane gels also containing only low molecular weight inert polysiloxanes. Other types of compatible solvents can be gelled by the zwitterionic silicone. Thus, a single solvent or a mixture of solvents may be used.

By solvent we mean (i) organic compounds, (ii) compounds containing a silicon atom, (iii) mixtures of organic compounds, (iv) mixtures of compounds containing a silicon atom, or (v) mixtures of organic compounds and compounds containing a silicon atom; used on and industrial scale to dissolve, suspend, or change the physical properties of other materials.

In general, the organic compounds are preferably inert aromatic hydrocarbons, aliphatic hydrocarbons, alcohols, aldehydes, ketones, esters, ethers, glycols, glycol ethers, alkyl halides, or aromatic halides. Representative of some common organic solvents are alcohols such as methanol, ethanol, 1-propanol, cyclohexanol, benzyl alcohol, 2-octanol, ethylene glycol, propylene glycol, and glycerol; aliphatic hydrocarbons such as pentane, cyclohexane, heptane, VM&P solvent, isoparaffinic solvents and mineral spirits; alkyl halides such as chloroform, carbon tetrachloride, perchloroethylene, ethylchloride and chlorobenzene; aromatic hydrocarbons such as benzene, toluene, ethybenzene and xylene; esters such as ethyl acetate, isopropyl acetate, ethyl acetoacetate, amyl acetate, isobutyl isobutyrate, and benzyl acetate; ethers such as ethyl ether, n-butyl ether, tetrahydrofuran, and 1,4-dioxane; glycol ethers such as ethylene glycol monomethyl ether, ethylene glycol monomethyl ether acetate, diethylene glycol monobutyl ether and propylene glycol monophenyl ether; ketones such as acetone, methyl ethyl ketone, cyclohexanone, diacetone alcohol, methyl amyl ketone, and diisobutyl ketone; petroleum hydrocarbons such as mineral oil, gasoline, naphtha, kerosene, gas oil, heavy oil, and crude oil; lubricating oils such as spindle oil and turbine oil; and fatty oils such as corn oil, soybean oil, olive oil, rape seed oil, cotton seed oil, sardine oil, herring oil and whale oil. "Other" miscellaneous organic solvents can also be used, such as acetonitrile, nitromethane, dimethlyisosorbide, dimethylformamide, propylene oxide, trioctyl phosphate, butyrolactone, furfural, pine oil, turpentine and m-creosol.

We further intend to encompass by the term solvent, volatile flavoring agents such as oil of wintergreen, peppermint oil, spearmint oil, menthol, vanilla, cinnamon oil, clove oil, bay oil, anise oil, eucalyptus oil, thyme oil, cedar leaf oil, oil of nutmeg, oil of sag, cassia oil, cocoa, licorice, high fructose corn syrup, citrus oils such as lemon, orange, lime and grapefruit, fruit essences such as apple, pear, peach, grape, strawberry, raspberry, cherry, plum, pineapple, and apricot, and other useful flavoring agents including aldehydes and esters such as cinnamyl acetate, cinnamaldehyde, eugenyl formate, p-methylanisole, acetaldehyde, benzaldehyde, anisic aldehydem citral, beral, decanal, vanillin, tolyl aldehyde, 2,6-dimethyloctanal, and 2-ethyl butyraldehyde.

In addition, we intend the term solvent to include volatile fragrances such as natural products and perfume oils. Some representative natural products and perfume oils are ambergris, benzoin, civet, clove, leaf oil, jasmine, mate, mimosa, musk, myrrh, orris, sandalwood oil, and vetivert oil, aroma chemicals such as amyl salicylate, amyl cinnamic aldehyde, benzyl acetate, citronellol, coumarin, geraniol, isobornyl acetate, ambrette, and terpinyl acetate; and the various classic family perfume oils such as the floral bouquet family, the oriental family, the chypre family, the woody family, the citrus family, the canoe family, the leather family, the spice family, and the herbal family.

Typically, we carry out the process using approximately a 1:1 molar ratio of the primary amine on the diamino containing polysiloxane and (A) itaconic acid or its ester derivative or (B) cyclic acid anhydride or (C) conjugated olefinic acids or mixtures of the same, preferably in the presence of a low molecular weight volatile methyl siloxane. Useful materials may also be prepared by carrying out the process with an excess of either the diamino containing polysiloxane or the acid containing reactant herein described with the caveat that a predominantly zwitterionic containing or mixed zwitterionic containing polymer is the resultant product. Mixed zwitterionic is defined herein as a polymer containing zwitterionic moieties, but having either an excessive anionic or cationic final charge. For instance, a 1:2 molar ratio of the primary amine on the diamino containing polysiloxane and (A) itaconic acid or its ester derivative and/or (C) conjugated olefinic acids will react to form useful materials since the secondary amine will be converted to a tertiary amine, which will be cationic below the isoelectric point. Corresponding products of (A) and (C) will be mixed zwitterionic with a net anionic charge. The resultant product's viscosity will be mildly to greatly reduced compared to that of the corresponding 1:1 ratio preparation. The remainder of the composition comprises the low molecular weight silicone oil or other solvent in amounts generally within the range of about 5–95 percent by weight of the composition, preferably about 75–95 percent by weight.

The viscoelastic zwitterionic silicone containing compositions of our invention have particular value in personal care formulations. Because of the unique volatility characteristics of the VMS component of these compositions, they can be used alone, or blended with other cosmetic fluids, to form a variety of over-the-counter (OTC) personal care products.

Thus, they are useful as carriers in antiperspirants and deodorants, since they leave a dry feel, and do not cool the skin upon evaporation. They are lubricious and can be used to improve the properties of skin creams, skin care lotions, moisturizers, facial treatments such as ache or wrinkle removers, personal and facial cleansers, bath oils, perfumes, colognes, sachets, sunscreens, pre-shave and after-shave lotions, liquid soaps, shaving soaps, and shaving lathers. They can also be used in hair shampoos, hair conditioners, hair sprays, mousses, permanents, depilatories, and cuticle coats, to enhance gloss and drying time, and provide conditioning benefits.

In cosmetics, they will function as dispersing, leveling and spreading agents for pigments in make-ups, color cosmetics, foundations, blushes, lipsticks, lip balms, eyeliners, mascaras, oil removers, color cosmetic removers, and powders. They are useful as controlled delivery systems for oil and water soluble substances such as vitamins. When incorporated into sticks, gels, lotions, aerosols, and roll-ons, the compositions impart a silky-smooth payout. Our viscoelastic zwitterionic silicone containing compositions have uses beyond the personal care arena, including, for example, as a filler or insulation material for electronics, electric cable and RTV fluids, a soil or water barrier for in-ground stabilization, or as a replacement for epoxy materials in the electronics industry.

They are also useful as carrier for cross-linked silicone rubber particles. In that application, (i) they allow ease of incorporation of the particles into such silicone or organic phases as sealants, paints, coatings, greases, adhesives, antifoams, and potting compounds; and (ii) they provide for modifying Theological, physical, or energy absorbing properties of such phases in either their neat or finished condition.

In addition, our viscoelastic zwitterionic silicone containing compositions are capable of functioning as carriers for pharmaceuticals, biocides, herbicides, pesticides, and other biologically active substances; and can be used to incorporate water and water-soluble substances into hydrophobic systems. Examples of some water-soluble substances are salicylic acid, glycerol, enzymes, and glycolic acid. For example, enzymes can be compounded in the silicone gel and admixed into harsh detergent systems to extend their active shelf life. Other variations may be made in compounds, compositions, and methods described herein without departing from the essential features of our invention. The forms of our invention are exemplary and not limitations on its scope as defined in the claims.

The following examples illustrate our invention in more detail.

EXAMPLE 1

Preparation of a trimethylsilyl capped diamino functional fluid having an average composition of $MD_{376}D'_{15}M$.

The following intermediates are combined:
1) 280 g. of DC 200 fluid 1000cS
2) 30.96 g. of aminoethylaminopropylmethyl-diethoxysilane (D')
3) 8.1 g water
4) 1.6 g KOH The mixture is heated slowly to 160° C. and volatiles are removed during this heat up period. This temperature is maintained for 6 hours. Upon cooling, 2 ml glacial acetic acid is added and stirred well into the reaction. The product is filtered leaving behind a clear viscous liquid with the following characterization:

Alkali # theory=55.36

Alkali # found=58.7

Equivalent weight=1911 g/eq.

EXAMPLE 2

Zwitterionic Polymer

Reaction of the Example 1 product ($MD_{376}D'_{15}M$) and itaconic acid, 20% weight in $D_5$.

The following intermediates are combined in a reaction vessel:

19.11 g. of silicone fluid from Example 1

1.3 g. itaconic acid 82 g. of decamethylcyclopentasiloxane ($D_5$)

The mixture is heated slowly to 115° C. with good agitation and held at 115° C. until all itaconic acid crystals are consumed. A noticeable increase in viscosity occurs upon cooling. The entire reaction mixture gelled but could be reversibly liquefied upon further heating.

EXAMPLE 3

Zwitterionic Polymer

Reaction of Example 1 product ($MD_{376}D'_5M$) with dodecenyl succinic anhydride.

The following intermediates are combined in a reaction vessel:

19.11 g. of silicone fluid from Example 1

2.66 g. dodecenyl succinic anhydride 87.08 g. of decamethylcyclopentasiloxane ($D_5$)

The silicone fluid and anhydride together represent 20% by weight in $D_5$.

The mixture is heated to about 50–60° C. A considerable viscosity increase is observed. The temperature is thereby maintained for ½ hour and then allowed to cool. A clear gel is obtained which would flow upon reheating.

EXAMPLE 4

Mixed Zwitterionic Polymer

Reaction of Dow Corning Q2-8220 pendant diamino siloxane (equivalent weight 3965) with two equivalents of acrylic acid (equivalent weight=72) in $D_5$ at 20% by weight non-volatile solids.

There are combined in a reaction vessel, 39.65 g of Q2-8220, (1.44 g of acrylic acid and 164 g of decamethylcyclopentasiloxane ($D_5$). The mixture is stirred and heated to about 125–130° C. and held for about 4 hours. A considerable viscosity build-up in the reaction mixture occurs upon cooling the mixture. Acid analysis of the mixture indicates the presence of only about 0.02% acrylic acid opposed to the initial concentration of 0.7%.

EXAMPLE 5

Mixed Zwitterionic Polymer

Reaction of Dow Corning Q2-8220 pendant diamino siloxane (equivalent weight 3965) with one equivalent dodecylsuccinic anhydride (DDSA) is added along with a quantity of $D_5$ sufficient to dilute the solids to 20% by wt. After completion of the reaction, an equivalent of itaconic acid is added.
Equivalent Weights of the Reactants Dow Corning Q2-8220=3965 (per pendant amino radical)

Dodecylsuccinic anhydride=266

Itaconic acid=130

The reactants are combined in a reaction vessel on a 0.01 molar basis in a reaction vessel in the following proportions:

Q2-8220=39.65 g.

DDSA=2.66 g

Total solids of the above ingredients of 43.61 g requires 20% solids concentration in a batch weighing 218 g. requires 174.44 g of decamethylcyclopentasiloxane ($D_5$).

Q2-8220, DDSA and $D_5$ are combined (alkali #=5.2) and heated to 60° C. for two hours. Alkali #=2.3

This suggests complete conversion because alkali # after first stage should=acid #;

$$(0.01)(45100 \text{ meq KOH})/(216.7 \text{ g})^* = 2.58$$

*Since itaconic has not been added yet, the total weight of 218−1.3=216.7. Next, 1.3 g itaconic acid is added and the reaction mixture is held at 115° C. for about two hours. When cool, the product mixture is a clear, viscous gel. A final acid number is 4.9 compared to 5.17 theory.

EXAMPLE 6

Zwitterionic Polymer

A mixture of 16.12 gms. of a pendant diamino α, ω-functional polysiloxane fluid available from Shin Etsu under the trade name KF857, 1.3 gms. of itaconic acid and 52.3 gms of $D_5$ are combined in a reaction vessel and heated to 115–120° C. for 2 hours. A reaction product which is a clear viscous fluid that solidified upon cooling is obtained. The reaction product has a 25% solids content and an alkali number of 8.4 and an acid value of 8.2.

EXAMPLE 7

Zwitterionic Polymer

Witco Silsoft® A-887 is a fairly low molecular weight pendant diamino capped polysiloxane with an equivalent weight of 3624 g/mol. 120.7 gms Silsoft A-887 was added to 375 gms DC-245 and reacted with one equivalent quantities or 4.3 gms. of itaconic acid for 2 hours at 125° C. and had a viscosity of 450 cP upon cooling. The reaction product has a 25% solids content and an alkali number of 4.2 and an acid value of 4.0.

EXAMPLE 8

Mixed Zwitterionic Polymer 116.4 gms Silsoft A-887 is added to 375 gms DC-245 and reacted with two equivalents or 8.6 gms. of itaconic acid for 2 hours at 125° C. The reaction product has a viscosity of 200 cP upon cooling. The reaction product has a 25% solids content and an alkali number of 3.65 and an acid value of 8.61.

EXAMPLE 9

Zwitterionic Polymer 241.4 gms Silsoft A-887 is added to 250 gms DC-245 and reacted with one equivalent quantity or 8.6 gms. of itaconic acid for 2 hours at 125° C. The reaction product has a viscosity in excess of 100,000 centi-Poise upon cooling, a 50% solids content, an alkali number of 8.2 and an acid value of 7.2.

EXAMPLE 10

Neat Zwitterionic Polymer

Neat reaction of Dow Corning Q2-8220 (described in example 5) with one equivalent of itaconic acid.

There are combined in a reaction vessel, 96.8 gms of Q2-8220 and 3.2 gms itaconic acid. The mixture is stirred and heated to about 125–130° C. and held for about 2 hours. A considerable viscosity build-up occurs during the heating phase. The cooled product is a clear hardened rubber with a viscosity >3.5 million centi-Poise, an alkali # of 14.3 and an acid value was 16.7.

EXAMPLE 11

Neat Zwitterionic Polymer

Neat reaction of Dow Corning Q2-8220 with two equivalents of itaconic acid.

There are combined in a reaction vessel, 93.7 gms of Q2-8220 and 6.3 gms itaconic acid. The mixture is stirred and heated to about 125–130° C. and held for about 2 hours. A considerable viscosity build-up occurs during the heating phase. The cooled product is a white gel with a viscosity ~500,00 centi-Poise, an alkali # of 8.9 and an acid value of 33.1. Comparison of example 10 to example 11 illustrates the optimum viscosity building characteristic of the 1:1molar ratio of primary amine to acid containing reactant.

EXAMPLE 12

Zwitterionic Polymer

A mixture of 18 gms (0.005 mole) KF-874 by Shin-Etsu, 1.75 gms octadecenyl succinic anhydride (ODSA) and 78.9 gms D5, representing a 20% active solution, is heated to 70° C. for one hour. The final product is a clear gel, having an alkali # of 2.3 (theoretical 2.8) and the acid value of 2.8. The final product was a clear gel.

EXAMPLE 13

Zwitterionic Polymer

A mixture of 18 gms (0.005 mole) KF-874, 1.5 gms dodecenyl succinic anhydride (DDSA) and 78.4 gms $D_5$, representing a 20% active solution, is heated to 50° C. for one hour. The product's alkali # is 2.5 and the acid value is 2.7. The final product is a clear thickened fluid of 23440 cP viscosity at 25° C.

EXAMPLE 14

Zwitterionic Polymer

A mixture of 18 gms (0.005 mole) KF-874 from Shin-Etsu, 1.75 gms octadecenyl succinic anhydride (ODSA), 39.45 gms of Isopar® M from Exxon and 39.45 gms $D_5$, representing a 20% active solution, is heated to 70° C. for one hour. The reaction product alkali # is 2.9 and the acid value is 3.0. The final product is a clear gel.

EXAMPLES 15–20

A sedimentation study in 100 ml graduated cylinders is run to determine the intrinsic value of our compositions for suspending or dispersing inorganic sunscreen, antiperspirant and pigments solids. The inventive polymer system of Example 7 is used in the preparation of the compositions of examples 18, 19 and 20. The inorganic sunscreen powder is alumina coated micronized $TiO_2$ from Uniq® called Uniq® UV1. The antiperspirant powder is REHEIS REACH®701 SUF (100%) and the pigment is Iron oxide PureOxy® Umber by Hilton Davis Co. Additional solvent was DC245 cyclomethicone by Dow Corning. The proportion of ingredients used and results of the tests are reported in Table 1, below.

TABLE 1

| Example | 15 | 16 | 17 | 18 | 19 | 20 |
|---|---|---|---|---|---|---|
| Uniq UV1 | 1 | — | — | 1 | — | — |
| Pure Oxy Umber | — | 1 | — | — | 1 | — |
| REACH 701 SUF | — | — | 1 | — | — | 1 |
| DC 245 | 99 | 99 | 99 | 89 | 89 | 89 |
| Product Example 7 | — | — | — | 10 | 10 | 10 |
| Total | 100 | 100 | 100 | 100 | 100 | 100 |
| Sedimentation Data | | | | | | |
| Start | none | none | none | none | none | none |
| 30 minutes | 98* | none | 2* | none | none | none |
| 1 day | full | none | full | none | none | none |
| 1 week | — | none | — | none | none | none |

*supernatant present (ml).

This data clearly shows that <2.5% of this novel polymer (on an active basis) is compatible with, or acts as a primary dispersing or suspending agent for, antiperspirant salts, $TiO_2$ and iron oxide powders. Optionally, other powders may include, but are not limited to, mica, ZnO and PTFE and derivatives thereof. Such systems may further employ one or more additional co-dispersants.

EXAMPLE 21

An antiperspirant is formulated with a ionically crosslinked composition of the invention combined and three other ingredients shown in Table 2 below. The antiperspirant product exhibits a high degree of spreadability, smoothness, little or no residue, and dryness, among its beneficial properties.

TABLE 2

| Ingredient | Amount |
|---|---|
| Estol 1543 (Emollient) | 6 parts |
| Product of EXAMPLE 2 | 70 parts |
| Antiperspirant Active | 23 parts |
| Fragrance | 1 part |

The composition is formed by mixing the materials with a rotary mixer at 65° C. and cooling to form a thickened product.

In table 2, the emollient Estol 1543 is octyl palmitate, an ester of 2-ethylhexyl alcohol and palmitic acid available from Uniqema. The antiperspirant active ingredients is Aluminum-Zirconium Tetrachlorolhydrex-Gly (CTFA INCI name) in the form of a super-fine micronized powder. However, the formulation may contain other antiperspirant salt actives such as Aluminum Dichlorohydrate, Aluminuin Sesquichlorohydrate, Aluminum-Zirconium Trichlorohydrex-Gly, Aluminum-Zirconium Pentachlorohydrex-Gly, or Aluminum-Zirconium Octachlorohydrex-Gly.

Formulated antiperspirants generally contain a maximum use level of antiperspirant salt active of 20% by weight aluminum-zirconium type and 25% by weight aluminum chlorohydrate type on an anhydrous basis.

Emollient oils other than octyl palmitate can be used in the formulation, such as mineral oil, peanut oil, sesame oil, avocado oil, coconut oil, cocoa butter, almond oil, safflower oil, corn oil cotton seed oil, castor oil, olive oil, jojoba oil paraffin oil. cod liver oil, palm oil, soybean oil, wheat germ oil, linseed oil, and sunflower seed oil; fatty acid esters such as isopropyl myristate, isopropyl palmirate, isopropyl stearate, butyl stearate, cetyl stearate, diisopropyl adipate, isodecyl oleate, diisopropyl sebacate, and lauryl lactate; fatty acids such as lauric, myristic, cetyl, palmitic, stearic, oleic, linoleic, and behenic acid; fatty alcohols such as lauryl, myristyl cetyl, stearyl isostearyl, oleyl, ricinoleyl erucyl, and 2-octyl dodecanol, alcohol; lanolin and its derivatives such as lanolin, lanolin oil, lanolin wax, lanolin alcohols, lanolin fatty acids, isopropyl lanolate, ethoxylated lanolin, and acetylated lanolin alcohols; and hydrocarbons such as petrolatum and squalane. Fragrances suitable for use in example 21 may include any of the natural products and perfume oils previously enumerated.

Optional ingredients may be used in conjunction with or can fully replace the antiperspirant salt to make a cosmetic gel or cream. Optional ingredients include: silicone compounds such as those previously enumerated and the like; crossliked gelled orgaopolysiloxanes such as dimethicone/vinyldimethicone crosspolymers; antimicrobial actives like triclosan; insect repellents, anti-fungal agents; sunscreens, vitamins; plant extracts; self-tanning actives like dihydroxyacetone; alternate solvents such as dimethylisosorbide and particulates like fumed silica or clays.

EXAMPLES 22–25

The products of this invention are surprisingly found to be film formers with exceptional adhesive properties towards keratin and other natural and synthetic surfaces. Use of compositions of the invention as components of a hair fixative/conditioner is illustrated below, as both a primary and as a secondary fixative ingredient. The instant invention includes, but is not limited to, the fixative examples below, additionally including those resins and additives known to one skilled in the art. The following two sets of fixative compositions are prepared and each applied to eight sets of bleached and permed brown hair (International Hair Importers & Products) and allowed to set for two hours. The formulations prepared in percent by weight and organoleptic test results are shown Table 3, below.

TABLE 3

|  | Example 22 | Example 23 | Example 24 | Example 25 |
|---|---|---|---|---|
| Product from Example 2 | 20.0 (4 gms. Active) | — | 5.0 (1 gm active) | — |
| DC 245 ® | 80.0 | 100.0 | — | 5.0 |
| Ethanol | — | — | 91.5 | 91.5 |
| Amphomer ® | — | — | 3.0 | 3.0 |
| AMP-95 ® (Angus) | — | — | 0.5 | 0.5 |
| Evaluation | # Panelists for example 22 | # Panelists for example 23 | # Panelists for example 24 | # Panelists for example 25 |
| Gloss | 8 | 0 | 7 | 1 |
| Stiffness | 8 | 0 | 4 | 4 |
| Dry comb | 3 | 5 | 8 | 0 |
| Anti-static | 3 | 5 | 7 | 1 |
| Curl Retention | 8 | 0 | 5 | 3 |

Examples 22 illustrates the primary fixative/conditioning properties of the invention compared to the cyclomethicone control, example 23, which does not act as a fixative. Gloss, Stiffness (fix), and curl retention (80% RH 25° C.) are all significantly improved. Additionally, the hair tresses treated with composition of Example 22 has a highly conditioned, emollient feel after comb out. A dry feel may also be obtained from a blend of commercially available fixative polymers and other additives. Amphomer®, INCI name octylacrylamide/acrylates/butylaminoethyl methacrylate copolymer from National Starch and Chemical, is a zwitterionic fixative known in the art for having excellent fixative properties and for being hard to dry comb when used alone. Surprisingly, Example 24 is equal in stiffness to Example 25, but is significantly improved in gloss, dry comb and anti-static properties.

EXAMPLES 26–28

Wet and wet-like cleaning wipes and similar articles are particularly useful in removing perianal and other skin soils. Recent U.S. patents such as U.S. Pat. Nos. 5,863,663, 5,763,332 and 5,756,112 disclose non-woven synthetic wipes and tissue paper web that is treated with a high internal water phase inverse emulsion made to break on rubbing. In particular, U.S. Pat. No. 5,756,112, used an organopolysiloxane-polyalkylene emulsifier, which stated better water retention and hand-feel aesthetics than organic emulsifiers. This patent additionally disclosed covalently crosslinked organopolysiloxane-polyalkylene emulsifiers for this application.

Surprisingly, the interfacial tension of non-covalently crosslinked products from the current invention revealed those products of equivalent weight less then 4000 g/mol begin to significant lower the interfacial activity between an oil phase like cyclomethicone and water. Significant interfacial activity of the lower equivalent weight derivatives suggests utility as a co-emulsifier. The water-oil interfacial activity of Q2-5200 is found to be 4.75 dynes/cm at 0.2% concentration in $D_5$. However, Q2-5200 is a mixture of dodecene, alkyl siloxane-copolyols and solvents which makes direct comparison to the current invention difficult.

In Table 4, below, a specific illustration of the preparation of wet-like cleaning wipes in accordance with the present invention by treating tissue paper webs with high internal phase water-in-lipid inverse emulsions.

TABLE 4

|  | Example 26 | Example 27 | Example 28 |
|---|---|---|---|
| Ceresine Wax (SP 252P, melt pt ~130° C.) | 6 | 6 | 6 |
| Arlacel ® P135 | 2 | 2 | 2 |
| Span ® 85 | 1 | 1 | 1 |
| Cyclomethicone D5 | — | — | 1 |
| Product of Example 12 | — | 1 | — |
| DI Water | 84 | 84 | 84 |
| NaCl | 7 | 7 | 7 |
| Test Results. | Example 26 | Example 27 | Example 28 |
| Emulsion Stability 25° C. | Stable | Stable | Stable |
| Hand Feel on Dry Down | Irregular | Smooth | Irregular |
| Shear required to Break emulsion | High | Medium | Medium |

Water-in-lipid emulsion is prepared from the proportion of ingredients in the table above using the following preparation: the aqueous phase is heated to 75° C. The remaining lipid phase ingredients (ceresine wax, $D_5$ and polymer) are heated, with mixing to a temperature of 75° C. until melted. The water phase is combined very slowly to the lipid phase and mixed under high shear with a flat blade stirrer. Mixing is continued until the water-in-lipid emulsion forms, as evidenced by a rapid increase in viscosity over 2000 centipoise as measured with a Brookfield RV-DV-II® viscometer. The emulsion can be applied to a substrate according to the methods known to those skilled in the art.

EXAMPLE 29

Skin Creme

The inventive products a re not water soluble, but can be emulsified by traditional techniques as part of the oil phase in either O/W or W/O emulsions. The HLB requirement of the oil phase is normally identified through use of standard mixtures of surfactants with known HLB values, for example, by using predetermined blends of SPAN® & TWEEN® from Uniqema, to find the most stable emulsion as shown in Table 5, below.

TABLE 5

| Skin crème formulation (HLB 8) | EXAMPLE 29 |
|---|---|
| Deionized water | 78% |
| Brij ® 72 | 1.4 |
| Brij 721 | 0.6 |
| Product of Example 7 (25% active) | 20 |

This emulsion passes HLB 8 screening stability and is stable for 15 minutes in a 5000 RPM centrifuge. Those skilled in the art can modify this formula to include many other functional attributes. Once emulsified and applied to a substrate, the novel polymer system forms a continuous film upon dry down and provides emolliency, gloss and water-resistance, among other attributes. Furthermore, a formulation sensitive active, including but not limited to, vitamin C, could first be incorporated in the novel polymer gel matrix and then emulsified by traditional methods to extend the shelf life of the active.

EXAMPLE 30

Shampoo

Two-in-one shampoos that include polydimethysiloxanes, or derivatives thereof, and deposition aids have been on the market for more than a decade. The novel silicone zwitterionic polymer system can be formulated into this class of shampoo as illustrated in Table 6, below, without difficulty to provide additional post setting and heat activated benefits.

TABLE 6

| Ingredients | % By Weight |
|---|---|
| DiWater | 25.55 |
| Celquat ® SC-240[1] (National Starch and Chemical Co) | 0.30 |
| Ammonium lauryl sulfate (28%) | 30.00 |
| Ammonium laureth-2 sulfate (26%) | 30.00 |
| Product from Example 7 | 2.00 |
| Monasil PLN (Uniqema) | 4.00 |
| Estol ® 3750 (Uniqema) | 2.00 |
| Cetearyl Alcohol | 1.00 |
| Monamid ® CMA[3] (Uniqema) | 3.00 |
| Phospholipid ® SV[4] (Uniqema) | 1.20 |
| Cetrimonium chloride | 0.75 |
| Fragrance | 0.20 |
| Total | 100.00 |

INCI names: [1]Polyquaterium-10, [2]Glycol Distearate, [3]Cocamide DEA, [4]Stearamidopropyl PG-Dimonium Chloride Phosphate (and) Cetyl Alcohol To water slowly add the Celquat SC-240 with high speed agitation while heating to 70° C. When the Celquat SC-240 is dissolved, add the ammonium lauryl sulfate and ammonium laureth sulfate with moderate agitation. Add product from example 7 to Monasil PLN, then add to batch. When temperature reaches 70° C. add Estol 3750, cetearyl alcohol and Monamid CMA, Add the Phospholipid SV and stir. Begin cooling to 50° C. then add the cetrimonium chloride. Add fragrance while cooling to room temperature.

This highly substantive formulation, example 30, is tested on damaged and permed hair and is found to provide excellent wet comb, build body (particularly after a heat treatment using a conventional hot air gun) and left the hair glossy and soft feeling. Monasil® PLN acts as a unique formulation aid by helping to emulsify the silicones while lowering the need for homogenization. Phospholipid SV functions as a novel silicone deposition aid.

EXAMPLE 31

Waterproof Coating

Color cosmetic, health and personal care preparations including, but not limited to, sunscreens, sunless tanners, eye liners, eye shadows, blushes, foundations, toners, mascaras, body or lip preparations and dermal or transdermal patches, frequently lose effectiveness, run or smear in the presence of water or simple mechanical abrasion. Industrial waterproof applications may include, but is not limited to, adhesives, coatings, paints, textiles, hard surface protection, corrosion protection, agricultural coatings, pesticides, insecticides, electronics and the like. It is desirable to be able to formulate products for such applications to be water-resistant, or more preferably water-proof, while also maintaining durability or resistance against nominal abrasive forces.

The waterproofing property of compositions of the invention on a keratin substrate is demonstrated using 4"×4" virgin wool swatches (#526 overcast stitched) obtained from Test Fabrics Inc, Middlesex N.J.

Two test swatches are first cleaned in isopropyl alcohol (IPA) to remove residual fatty soils, like lanolin, and then completely dried and tare weight recorded. Next, one of the swatches, sample 31a, is immersed in the product of sample 13 and removed. The other swatch, sample 31-b, is immersed only in $D_5$ cyclomethicone. Both swatches are dried at 45 degrees centigrade for 18 hours to ensure complete volatilization of the D5 cyclomethicone. Swatch weight is recorded at room temperature after the 18 hour drying step. Weight gain is reported in percent over the weight of the untreated swatch: (31a) 2.3% and (31b) 0%.

A 0.1% active surfactant solution is prepared using Monawet® MO-70R, dioctyl sodium sulfosuccinate (from Uniqema). This solution is known in the art as expediting wetting of textiles and others substrates. A 0.5 ml. aliquat of the wetting solution is applied to the center of each test swatch and the time required for the wetting solution to visually "wet" the clothes are as follows: (31a)>3 hours (water began evaporating off swatch); (31b) 5 minutes. In conclusion, less than 2.3% polymer on an active basis is required to completely water-proof a protein substrate such as keratin/wool. However, water-proofing is applicable to other substrates because water-proofing generally is considered a property of the compositions of the present invention, since this property is related to increasing ionic cross-link density upon solvent evaporation. This particular example is illustrative of the novel waterproofing compositions and methods that can be achieved by combining pendant zwitterionic grafts on an $\alpha,\omega$-alkoxy-functional polydimethyl siloxanes.

EXAMPLE 32

Sunscreen

In Table 7, below, is an example of a W/O emulsion containing sunscreen and the product of example 7, compared to a control sample.

TABLE 7

| | Control % by weight | Example 32 % by weight |
|---|---|---|
| Phase I | | |
| Deionized water | 81.8 | 81.8 |
| magnesium sulfate | 0.7 | 0.7 |
| Phase II | | |
| Cyclomethicone D5 | 10.0 | 2 |
| Span 85 | 1 | 1 |
| Example 7 (25% polymer) | 0 | 8 |
| Arlacel P135 | 0.5 | 0.5 |
| Ethyl hexyl p methoxycinnmate | 3 | 3 |
| Octyl stearate | 3 | 3 |

Emulsion procedure: Heat the water and $MgSO_4$ to 75° C. Combined the oils (phase II) and heat to 85° C. Add the water to the oils very slowly with good agitation. Homogenize and cool. Test products are applied sparingly to glass plates and allowed to dry. Each plate is immersed in water for 20 minutes, pulled out of the water for 20 minutes, put in water for 20 minutes, out water for 20 minutes, for 80 Minutes total. The plates are allowed to dry and then misted with ~1 g. deionized water. The plate treated with example 32, the inventive polymer, beaded water to a larger extent than the cyclomethicone control sample at the end of the test and is therefore more water-resistant.

Water-resistant sun care formulations containing the inventive polymer system can also contain inorganic sun filters, such as TiO$_2$ or ZnO (available in powdered or dispersed form). The inorganic filters can be used singularly or in combination (i.e.TiO$_2$ and ZnO blends) and may also be used in conjunction with organic sun filters, in this or other emulsion or solution based formulations known to those skilled in the art.

EXAMPLE 33

Car Wax Application

The durability of a uniform film-former is related, in part, to adhesion to a particular substrate, intrinsic film toughness and general environmental resistance. Many commercial car wax preparations containing silicones utilize mixtures of amino-functional siloxanes such as SF 1705 and SF 1706 (GE Silicones, Waterford N.Y.) to increase depth of gloss, ease of rub-on/off and add durability to repeated environmental insults consisting of washing, rain and road salts.

The model test described in detail below was developed to screen commercial and experimental waxes for resistance to rain and car washes. In particular, the car wash mode test was to be severe enough that only one commercial wax/polish was found able to pass more than one cycle.

| | Durability Test (Pass/Fail) | |
|---|---|---|
| Commercial Product Tested | Water 5x | Alcojet ® 1x |
| Turtle Wax ® | Pass | Fail |
| Rain Dance ® | Pass | Fail |
| Rally ® | Pass | Fail |
| Zymol ® | Pass | Pass* |
| Black Magic Body Wet ® | Pass | Fail |
| Nu Finish ® | Pass | Fail |
| Finish 2001 ® | Fail | Fail |
| Mequiars ® | Pass | Fail |

*also passed 3 cycles

Test procedure:

An oxidized car hood is divided into 4×6 inch test panels. Panels are washed with a 0.3% active sodium lauryl sulfate solution, rinsed and then dried. Prior to wax application, each panel is first misted with deionized water to assure that water did not bead up on the panel surface. Panels are dried and a test product is applied by rubbing each panel using a cloth containing excess (~1 g) test product. The panels are air-dried for 30 minutes, buffed out for one minute and the complete application cycle repeated 1×. Initial gloss is determined as poor, moderate, good or excellent. Panels are then placed in a household automatic dishwasher face down and washed without detergent for 5 full cycles. The panels are removed when dry, placed treated side up on a table and uniformly sprayed with ~1 gram water. Test panels that uniformly beaded water passed. Test panels passing the 5-cycle water test are placed back into the automatic dishwasher and washed 1 cycle using 70 g. Alcojet (low-foaming powdered detergent available from Alconox, Inc. New York, N.Y.), and reevaluated for water beading.

Those passing 1 cycle could then be subsequently tested using additional cycles of washing and evaluated.

In Table 8, below, is listed the proportion of ingredient used in the preparation of experimental car wax formulations.

TABLE 8

| Ingredients | Control 33A Amino-functional control | Control 33B carboxy-functional control | Example 33A Inventive Zwitterionic functional | Example 33B Inventive Zwitterionic functional |
|---|---|---|---|---|
| GE SF 1705 (aminosiloxane) | 3 | — | — | — |
| GE SF 1706 (aminosiloxane) | 1.5 | — | — | — |
| Monasil PCA 100% active | — | 4.5 | — | — |
| Product of Example 14 | — | — | 22.5 | — |
| Product of Example 10 | — | — | — | 4.5 |
| DC200 fluid (12,500 cSt) | 2 | 2 | 2 | 2 |
| Carnauba #1 Wax (Ross Wax) | 6 | 6 | 2 | 6 |
| Actinol ® FA-2 (Arizona Chemical) | 3 | 3 | 3 | 3 |
| Isopar ® H (Exxon) | 24 | 24 | 6 | 24 |
| Water | 53 | 53 | 53 | 53 |
| Kapolite SF (Kapolite Inc.) | 7 | 7 | 7 | 7 |
| TEA | 0.5 | 0.5 | 0.5 | 0.5 |
| Results | | | | |
| Rub-Off | Good | Poor | Fair | Good |
| Depth of gloss | Good | Good | Good | Excellent |
| Water Wash 5x | Pass | Pass | Pass | Pass |
| Auto Alcojet Test 1x | Fail | Pass | Pass | Pass |
| Auto Alcojet Test 3x | Fail | Fail | Pass | Pass |

Incorporation of the commercial carboxylic acid functional siloxane, Monasil PCA (PCA dimethicone, Uniqema, Wilmington Del.) in place of the aminofunctional siloxanes from GE (Control 33A) improved 1 wash Alcojet resistance. However, only formulations containing the zwitterionic-functional polymers of the current invention (Example 33A and Example 33B) unexpectedly passed the 3 cycle test, illustrating novel durability attributes. This particular example is relevant to low-VOC applications since it uses only 6% VOC's. As in the waterproofing example, Example 31, other substrates are applicable because durability is considered a general property of this invention since it is related to increasing ionic cross-link density upon solvent evaporation.

What is claimed is:

1. A method of preparing an ionically cross-linked composition of a thickened gel-like consistency comprising reacting (A) a diamino containing polysiloxane of the general formula:

Formula 1

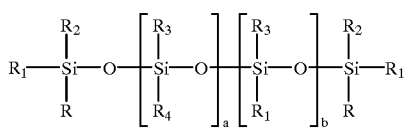

wherein:

R, which can be the same or different, is selected from R$_2$ or —OR$_9$, wherein R$_9$ is hydrogen or alkyl;

R₁ can be the same or different and is selected from R, R₂ and a diamino containing radical of the formula —F₁—NR₅—F—NH₂; with the proviso that at least one R₁ group is a diamino containing radical wherein; F₁ is linear or branched alkylene of 1–12 carbon atoms; F is linear or branched alkylene of 1–10 carbon atoms; and R₅ is hydrogen or lower alkyl;

R₂ can be the same or different and is selected from R or substituted or unsubstituted alkyl, aryl and olefinic (vinyl);

R₃ and R₄, which can be the same or different, are selected from substituted or unsubstituted alkyl, aryl, capped or uncapped polyoxyalkylene, alkarylene, aralkylene or alkenyl;

a is an integer from 0 to 10,000; and b is an integer from 10 to 1000; with the proviso that when a pendant R₁ group is a diamino containing radical, a can be 0 or a and b are present in the ratio of a:b of at least 1:1 to about 200:1;

with (B), an acid containing reactant selected from itaconic acid and/or the trialkylsilyl ester derivatives thereof; substituted or unsubstituted cyclic acid anhydride; substituted or unsubstituted conjugated olefinic acid and mixtures of the same at an elevated temperature in the presence of (C) a low molecular weight silicone oil or other solvent for a time sufficient to form an ionically cross-linked zwitterionic siloxane polymer of a gel-like consistency containing both carboxylic acid and secondary and/or tertiary amino radicals.

2. The method of preparing an ionically cross-linked composition as claimed in claim 1, wherein said acid containing reactant is itaconic acid, the trialkylsilyl radical ester derivative of itaconic acid or mixtures of the same.

3. The method of preparing an ionically cross-linked composition as claimed in claim 1, wherein said substituted or unsubstituted cyclic acid anhydride reactant is selected from the group of consisting of succinic anhydride, maleic anhydride, phthalic anhydride, itaconic anhydride, octenyl succinic anhydride, dodecenyl succinic anhydride, and octadecenyl succinic anhydride.

4. The method of preparing an ionically cross-linked composition as claimed in claim 1, wherein said substituted or unsubstituted conjugated olefinic acid is an unsaturated carboxylic acid.

5. An ionically cross-linked polysiloxane composition comprising at least about 5% by weight of a low molecular weight silicone oil or other solvent and a zwitterionic siloxane polymer composition comprising an ionically cross-linked composition component of a thickened gel-like consistency represented by the formula Formula 2

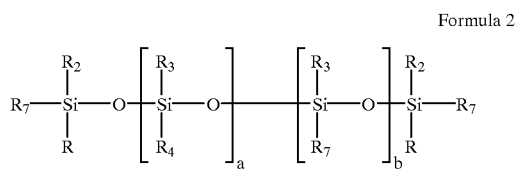

wherein:

R, which can be the same or different, is selected from R₂ or —OR₉, wherein R₉ is hydrogen or alkyl;

R₁ can be the same or different and is selected from R, R₂ and a diamino containing radical of the formula —F₁—NR₅—F—NH₂; with the proviso that at least one R₁ group is a diamino containing radical wherein; F₁ is linear or branched alkylene of 1–12 carbon atoms; F is linear or branched alkylene of 1–10 carbon atoms; and R₅ is hydrogen or lower alkyl;

R₂ can be the same or different and is selected from R or substituted or unsubstituted alkyl, aryl and olefinic (vinyl);

R₃ and R₄, which can be the same or different, are selected from substituted or unsubstituted alkyl, aryl, capped or uncapped polyoxyalkylene, alkarylene, aralkylene or alkenyl;

a is an integer from 0 to 10,000; and b is an integer from 10 to 1000; with the proviso that when a pendant R₁ group is a diamino containing radical, a can be 0 or a and b are present in the ratio of a:b of at least 1:1 to about 200:1;

R₇, which can be the same or different, is selected from R₁ or a group selected from (a), (b) or (c) below, with the proviso that at least one R₇ group is selected from:

(a) a pyrrolidone containing group of the general structure represented by the formula 3 if about one equivalent of itaconic acid or ester thereof is reacted with the primary amine of the diamine group:

Formula 3

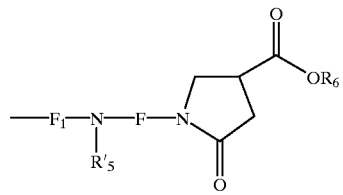

wherein:

R'₅ is hydrogen lower alkyl or a group represented by Formula 3a, with the proviso that if more than one equivalent of itaconic acid or ester thereof was charged to the reaction mixture containing formula 1, R'₅ can include a group represented by Formula 3a:

Formula 3a

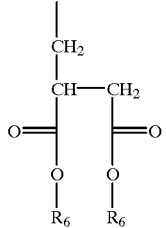

wherein:

R₆ is OH, OM or trialkylsiloxy, wherein M is a cation selected from an alkaline earth metal, alkali metal, ammonium or substituted ammonium salt;

F₁ is linear or branched alkylene of 1–12 carbon atoms; and

F is linear or branched alkylene of 1–10 carbon atoms (b) a group of the general structure represented by Formula 4, if about one equivalent of a cyclic anhydride reactant is used;

Formula 4

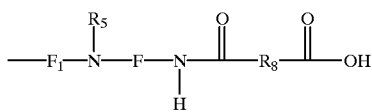

wherein:
$R_8$ is a substituted or unsubstituted, branched or unbranched alkylene radical;
$R_5$ is hydrogen or lower alkyl; and
$F_1$ and F are as hereinabove defined; and
(c) a group of the general structure of Formula 5 if about one equivalent of conjugated olefinic acid is used;

Formula 5

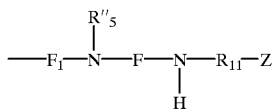

wherein:
$R''_5$ is hydrogen, lower alkyl or a group represented by Formula 5a with the proviso that if more than one equivalent of conjugated olefinic acid was charged to the reaction mixture containing formula 1, $R''_5$ is a group represented by Formula 5a;

  Formula 5a wherein:
$R_{11}$ is ethylene or substituted ethylene;
Z is —$CO_2H$ or —$SO_3H$; and
F and $F_1$ are as hereinabove defined.

6. The ionically cross-linked polysiloxane composition as claimed in claim 5, wherein group $R_7$ of the composition represented by Formula 2 is selected from $R_1$ or a group from (a) with the proviso that at least one $R_7$ group is a group from (a).

7. The ionically cross-linked polysiloxane composition as claimed in claim 5, wherein at least one $R_7$ group is a group from (a) and wherein $R^1_5$ is hydrogen or lower alkyl.

8. The ionically cross-linked polysiloxane composition as claimed in claim 5 which comprises at least about 5% by weight of a low molecular weight silicone oil.

9. The ionically cross-linked polysiloxane composition as claimed in claim 7 which comprises at least about 5% by weight of a low molecular weight silicone oil.

10. The ionically cross-linked polysiloxane composition as claimed in claim 7, wherein a and b are present in the ratio of a:b of from about 15:1 to about 25:1.

11. The ionically cross-linked polysiloxane composition as claimed in claim 7 which comprises from about 95% to 75% by weight of a low molecular weight silicone oil or other solvent.

12. A cosmetic material selected from the group consisting of hair fixatives, hair and body shampoos, skin cremes and lotions, antiperspirants, deodorants, sunscreens, self-tanners, lip preparations, personal wipes, dermal or transdermal patches and color cosmetics comprising an ionically cross-linked polysiloxane as claimed in claim 5.

13. The cosmetic material as claimed in claim 12, wherein said cosmetic material comprises the composition as claimed in claim 6.

14. The cosmetic material as claimed in claim 12, wherein said cosmetic material comprises the composition as claimed in claim 7.

15. A coating material for metallic and non-metallic substrates comprising the ionically cross-linked polysiloxane compositions as claimed in claim 5.

16. The coating material for metallic and non-metallic substrate as claimed in claim 15 wherein said composition comprises the composition as claimed in claim 6.

* * * * *

UNITED STATES PATENT AND TRADEMARK OFFICE
CERTIFICATE OF CORRECTION

PATENT NO.   : 6,124,490
DATED        : September 26, 2000
INVENTOR(S)  : Gormley, Berger and Fost It is certified that error appears in the above-identified patent and that said Letters Patent is hereby corrected as shown below:

Column 2,
Line 2, after "alkyl" insert -- or $OR_9$, wherein $R_9$ is hydrogen or alkyl, --.
Line 23, cancel "$R_2$" and insert -- substituted or unsubstituted alkyl --.
Line 35, cancel "R, and".

Column 4,
Line 23, cancel "or $SO_3H$".

Column 5,
Line 46, cancel "$R_2$" and insert -- substituted or unsubstituted alkyl --.
Line 57, cancel "R or".
Line 57, insert after "alkyl" -- or $OR_9$, wherein $R_9$ is hydrogen or alkyl, --.

Column 7,
Line 59, cancel "or $SO_3H$".

Column 24,
Line 4, cancel "R or".
Line 5, insert after "alkyl" -- or $OR_9$, wherein $R_9$ is hydrogen or alkyl, --.
Line 66, cancel "$R_2$" and insert -- substituted or unsubstituted alkyl --.

Column 27,
Line 34, cancel "or $SO_3H$".

Signed and Sealed this

Twelfth Day of November, 2002

*Attest:*

JAMES E. ROGAN
*Attesting Officer*    *Director of the United States Patent and Trademark Office*

UNITED STATES PATENT AND TRADEMARK OFFICE
CERTIFICATE OF CORRECTION

PATENT NO.   : 6,124,490
DATED        : September 26, 2000
INVENTOR(S)  : Gormley, Berger and Fost It is certified that error appears in the above-identified patent and that said Letters Patent is hereby corrected as shown below:

Column 2,
Line 2, after "alkyl" insert -- or $OR_9$, wherein $R_9$ is hydrogen or alkyl, --.
Line 23, cancel "$R_2$" and insert -- substituted or unsubstituted alkyl --.
Line 35, cancel "R, and".

Column 4,
Line 23, cancel "or $SO_3H$".

Column 5,
Line 46, cancel "$R_2$" and insert -- substituted or unsubstituted alkyl --.
Line 57, cancel "R or".
Line 57, insert after "alkyl" -- or $OR_9$, wherein $R_9$ is hydrogen or alkyl, --.

Column 7,
Line 59, cancel "or $SO_3H$".

Column 24,
Line 4, cancel "R or".
Line 5, insert after "alkyl" -- or $OR_9$, wherein $R_9$ is hydrogen or alkyl, --.
Line 66, cancel "$R_2$" and insert -- substituted or unsubstituted alkyl --.

Column 25,
Line 8, cancel "R or".
Line 9, insert after "alkyl" -- or $OR_9$, wherein $R_9$ is hydrogen or alkyl, --.

UNITED STATES PATENT AND TRADEMARK OFFICE
CERTIFICATE OF CORRECTION

PATENT NO. : 6,124,490
DATED : September 26, 2000
INVENTOR(S) : Gormley, Berger and Fost It is certified that error appears in the above-identified patent and that said Letters Patent is hereby corrected as shown below:

Column 27,
Line 34, cancel "or $SO_3H$".

This certificate supersedes Certificate of Correction issued November 12, 2002.

Signed and Sealed this

Twenty-first Day of January, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,124,490
DATED : September 26, 2000
INVENTOR(S) : Gormley, Berger and Fost It is certified that error appears in the above-identified patent and that said Letters Patent is hereby corrected as shown below:

Column 2,
Line 23, cancel "$R_2$" and insert -- substituted or unsubstituted alkyl --.
Line 35, cancel "R, and".
Line 35, after "alkyl" insert -- or $OR_9$, wherein $R_9$ is hydrogen or alkyl --.

Column 5,
Line 46, cancel "$R_2$" and insert -- substituted or unsubstituted alkyl --.
Line 57, cancel "R or".
Line 57, insert after "alkyl" -- or $OR_9$, wherein $R_9$ is hydrogen or alkyl, --.

Column 24,
Line 66, cancel "$R_2$" and insert -- substituted or unsubstituted alkyl --.

Column 25,
Line 8, cancel "R or".
Line 9, insert after "alkyl" -- or $OR_9$, wherein $R_9$ is hydrogen or alkyl, --.

This certificate supersedes Certificate of Correction issued January 21, 2003.

Signed and Sealed this

Twenty-seventh Day of May, 2003

JAMES E. ROGAN
*Director of the United States Patent and Trademark Office*